United States Patent
Massmann et al.

(10) Patent No.: US 6,734,142 B2
(45) Date of Patent: May 11, 2004

(54) AMMONIUM GLYPHOSATE COMPOSITIONS AND PROCESS FOR THEIR PREPARATION

(75) Inventors: Brent D. Massmann, Ballwin, MO (US); John T. Wang, St. Louis, MO (US); Dwane H. Campbell, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/122,806

(22) Filed: Apr. 15, 2002

(65) Prior Publication Data

US 2002/0173423 A1 Nov. 21, 2002

Related U.S. Application Data

(60) Provisional application No. 60/285,731, filed on Apr. 23, 2001.

(51) Int. Cl.[7] ............................................. A01N 57/02
(52) U.S. Cl. ................................................... 504/206
(58) Field of Search ........................................ 504/206

(56) References Cited

U.S. PATENT DOCUMENTS

| | | |
|---|---|---|
| 3,671,612 A | 6/1972 | Roszinski et al. |
| 4,405,531 A | 9/1983 | Franz |
| 4,840,659 A | 6/1989 | Franz |
| 5,047,079 A | 9/1991 | Djafar et al. |
| 5,070,197 A | 12/1991 | Chin et al. |
| 5,266,553 A | 11/1993 | Champion et al. |
| 5,324,708 A | 6/1994 | Moreno et al. |
| 5,410,075 A | 4/1995 | Moreno et al. |
| 5,430,005 A | 7/1995 | Kassebaum et al. |
| 5,612,285 A | 3/1997 | Arnold |
| 5,614,468 A | 3/1997 | Kramer et al. |
| 5,633,397 A | 5/1997 | Gillespie et al. |
| 5,656,572 A | 8/1997 | Kuchikata et al. |
| 5,693,593 A | 12/1997 | Arnold |
| 5,716,903 A | 2/1998 | Kramer et al. |
| 6,448,434 B1 | 9/2002 | Kramer |

FOREIGN PATENT DOCUMENTS

| | | |
|---|---|---|
| EP | 0 238 240 A2 | 9/1987 |
| EP | 0 378 985 A1 | 7/1990 |
| EP | 0 394 211 A1 | 10/1990 |
| EP | 0 256 608 B1 | 4/1992 |
| EP | 0 582 561 A1 | 2/1994 |
| FR | 2 692 439 A1 | 12/1993 |
| WO | WO 87/04595 | 8/1987 |
| WO | WO 90/07275 | 7/1990 |
| WO | WO 92/12637 | 8/1992 |
| WO | WO 92/18513 | 10/1992 |
| WO | WO 94/10844 | 5/1994 |
| WO | WO 96/40696 | 12/1996 |
| WO | WO 96/40697 | 12/1996 |
| WO | WO 01/08492 A1 | 2/2001 |

OTHER PUBLICATIONS

International Search Report for Application No. PCT/US 00/20337, dated Nov. 15, 2000, 3 pages.

Primary Examiner—S. Mark Clardy
(74) Attorney, Agent, or Firm—Senniger, Powers, Leavitt & Roedel; Joseph A. Schaper (57) ABSTRACT

A process is provided for preparing a downstream processable ammonium glyphosate paste. The process includes mixing in a reactor (i) particulate glyphosate acid, (ii) ammonia, (iii) adjuvant, and (iii) water. The reaction of glyphosate acid with ammonia causes the generation of heat resulting in the partial evaporation of the water such that an ammonium glyphosate paste is formed, having a moisture content of about 2% to about 20% by weight. The addition of the adjuvant to the reactor (i) increases the rate at which the glyphosate acid and ammonia react to form ammonium glyphosate and/or (ii) reduces the flow resistance of the reaction mass as it is being conveyed to the product discharge region of the reactor. The ammonium glyphosate paste may then be further processed to form a granular herbicidal composition.

127 Claims, 4 Drawing Sheets

AMMONIUM GLYPHOSATE COMPOSITIONS AND PROCESS FOR THEIR PREPARATION

REFERENCE TO RELATED APPLICATION

This application claims priority from U.S. provisional application Serial No. 60/285,731, filed on Apr. 23, 2001, the entire disclosure of which is incorporated herein by reference.

FIELD OF THE INVENTION

The present invention relates to preparation of a herbicidal formulation useful in agriculture and in other situations where control of weeds or other vegetation is desired. In particular, it relates to a process for preparing a herbicidal composition containing as an active ingredient N-phosphonomethylglycine (glyphosate) in the form of the ammonium salt thereof. According to the process of the present invention, particulate glyphosate acid, ammonia, and water react to form an ammonium glyphosate paste, and as part of the process a surfactant is added to the reaction mixture to increase the reaction rate and enhance the physical properties of the resulting product.

BACKGROUND OF THE INVENTION

Glyphosate herbicides, especially herbicides comprising a water-soluble salt of glyphosate, are well known. The monoammonium salt of glyphosate is disclosed as a useful herbicide for example in U.S. Pat. No. 4,405,531 issued to Franz. Unless the context demands otherwise, "ammonium glyphosate" herein refers to the monoammonium salt of glyphosate, which has the chemical formula Ammonium glyphosate may be produced in granular form by a continuous process in which glyphosate acid is intimately mixed with ammonia. For example, U.S. Pat. No. 5,070,197 issued to Chin et al. disclose a continuous process in which a Bronsted acid is mixed with a Bronsted base in an extruder to produce a salt. Chin et al. list glyphosate acid as one of the potential Bronsted acids that may be used and ammonia as one of the potential bases that may be used. According to Chin et al., the reaction may be carried out as a solid-state reaction essentially without addition of "extraneous solvent" such as water, although it is stated that a small amount of water (usually about 4% by weight) may be optionally added upstream for "initial lubricity". An acid-base reaction is said to occur in the extruder, forming a dry salt which is extruded to form granules.

Ammonium glyphosate is particularly useful, however, in the preparation of dry glyphosate herbicide formulations which contain one or more surfactants in addition to the glyphosate salt. Surfactants are important components of glyphosate formulations because when a glyphosate formulation is diluted, dissolved or dispersed in water for application by spraying to foliage of plants, the surfactants enhance the herbicidal effectiveness of the glyphosate spray by assisting in: (i) the retention of droplets of the spray by the foliage; (2) the adhesion of the spray droplets to the foliar surface; and, (3) the penetration of the glyphosate through the hydrophobic cuticle that covers the foliar surface. Commercially available dry ammonium glyphosate formulations containing one or more surfactant(s) include, for example, Roundup® Dry, Roundup® Max and Rival® herbicides, marketed by Monsanto Company in several countries.

Processes for producing dry ammonium glyphosate formulations typically require combining one or more surfactant(s) with a dry ammonium glyphosate salt and granulating the mixture to form dry ammonium glyphosate granules having the desired concentration of surfactant. Numerous granulation processes have been disclosed that are suitable for preparing water-soluble or water-dispersible granules of ammonium glyphosate with a liquid surfactant. One such process is pan granulation. However, a more widely used granulation process for a dry ammonium glyphosate formulation is extrusion granulation. British Patent No. 1 433 882 ("the '882 patent") generally describes an extrusion granulation process, and the granulation of dry ammonium glyphosate formulations are typically carried out in a similar process except that the primary active ingredient, namely ammonium glyphosate, is water-soluble rather than water-insoluble as in the process of the '882 patent. In this process, ammonium glyphosate is mixed with surfactant and a small amount of water to form an extrudable wet mix, which is then extruded to form strands of extrudate that break spontaneously at the point of extrusion or shortly thereafter to form short cylindrical granules, which are then dried.

The desired amount of surfactant for delivering the desired herbicidal effectiveness may be typically in the range of about 0.1 to about 1 part by weight of surfactant per part by weight of glyphosate, expressed as acid equivalent (a.e.), depending on the particular surfactant used. Ammonium glyphosate formulations having such a high concentration of surfactants may be difficult to achieve depending on the degree to which the surfactant is absorbed or adsorbed by the ammonium glyphosate. That is, frequently such high surfactant concentrations do not sufficiently absorb and/or adsorb to the ammonium glyphosate thereby causing the resulting formulation to become sticky, have a tendency to cake, or lack good pouring or flow properties. Thus, the absorbency and adsorbency properties of the ammonium glyphosate particles are especially important.

The process by which ammonium glyphosate is prepared has been found to affect the absorptive and/or adsorptive properties of the ammonium glyphosate particles with respect to a liquid surfactant. Recently, processes for producing a dry glyphosate powder having high absorptive and/or adsorptive characteristics suitable for producing ammonium glyphosate formulations having a high concentration of surfactant have been discovered. For example, U.S. Pat. No. 5,614,468 ("the '468 patent"), Kramer et al. disclose processes wherein particulate glyphosate acid is reacted with aqueous ammonia to produce a dry glyphosate powder having a moisture content of no greater than about 2% by weight of water. Similarly, U.S. Pat. No. 5,633,397 ("the '397 patent"), Gillespie et al., disclose a process for producing ammonium glyphosate powder wherein particulate glyphosate acid is reacted with gaseous anhydrous ammonia to produce a dry powder. As shown in Example 1 of the '397 patent, a dry powder having a moisture concentration of about 1% by weight may be produced by the process disclosed therein.

Both the process disclosed in the '468 patent and the process disclosed in the '397 patent produce a dry ammonium glyphosate powder capable of adsorbing and/or absorbing high concentrations of surfactant. However, dry solid-state reaction processes wherein the moisture content is suppressed to ensure the formation of a dry product may be more difficult to control than a process wherein glyphosate and ammonia are reacted in an aqueous medium. The exothermic nature of the reaction between ammonia and glyphosate acid gives rise to a need for the dissipation of heat, which can present problems. Since solid-state processes typically exhibit poor heat transfer properties, the dissipation of heat may become problematic.

PCT Application No. WO 01/08492, Massmann et al. disclose a process for producing ammonium glyphosate which avoids some of the difficulties encountered with processes carried out in a dry solid-state medium. Particulate glyphosate acid, ammonia in the form of either gaseous anhydrous ammonia or aqueous ammonia and water are added to a reactor to from a reaction mixture having a moisture content of about 10% to about 25% by weight. The glyphosate acid and ammonia react and a portion of the water is evaporated to produce a downstream processable ammonium glyphosate paste having a moisture content of about 5% to about 20% by weight. A surfactant is then mixed with the ammonium glyphosate paste prior to extrusion granulation, in part to condition the paste to improve the extrudability of the paste, but primarily to improve the herbicidal efficacy of the final ammonium glyphosate granules. According to Massmann et al., adding surfactant prior to or during the reaction process is detrimental to the process; thus, the entire amount of surfactant is added to the ammonium glyphosate paste after the entire reaction has been completed and preferably after the ammonium glyphosate paste has been cooled to less than 70° C.

SUMMARY OF THE INVENTION

Among the objects of the present invention is the provision of a continuous process for preparing a moist ammonium glyphosate paste; the provision of such a process wherein one or more adjuvant(s) are added to the reaction mixture to improve the rate of formation of the ammonium glyphosate paste and/or reduce the flow resistance of the reaction mixture; the provision of such a process wherein an additional quantity of adjuvant is subsequently added to the ammonium glyphosate paste to form an extrudable ammonium glyphosate mixture; the provision of such a process wherein the extrudable ammonium glyphosate mixture is extruded to form ammonium glyphosate granules; the provision of an improved process for extruding ammonium glyphosate having increased throughput; and, the provision of a process for extruding ammonium glyphosate having reduced power requirements.

Briefly, therefore, the present invention is directed to a process for preparing an ammonium glyphosate paste, comprising mixing in a reactor (i) particulate glyphosate acid, (ii) ammonia, (iii) water and (iv) adjuvant to form a reaction mass wherein the total amount of water added to the reaction mass is from about 10% to about 25% by weight of all of the glyphosate acid, ammonia, water and adjuvant added to the reactor.

The present invention is further directed to a continuous process for preparing an ammonium glyphosate paste, comprising continuously feeding to a reactor (i) particulate glyphosate acid, (ii) ammonia, (iii) adjuvant, and (iv) water, thereby causing a reaction of the glyphosate acid and ammonia generating heat which causes partial evaporation of the water, and forms an ammonium glyphosate paste having a moisture content of less than about 20% by weight. In a preferred embodiment, the moisture content will fall within the range of from about 2% to about 15% by weight.

The present invention is further directed to a continuous process for preparing a granular herbicidal composition, comprising continuously feeding (i) particulate glyphosate acid, (ii) ammonia, (iii) adjuvant, and (iii) water to form a reaction mass in which ammonium glyphosate is formed, wherein the amount of water fed is from about 10% to about 25% by weight of all materials being fed to the reactor. The reaction of glyphosate acid and ammonia generates heat, causing the evaporation of water such that the water content of the reaction mass is reduced to from about 2% to about 10% to form an ammonium glyphosate paste. The reaction mass is continuously conveyed to the product discharge region of the reactor and as part of the process, the adjuvant (i) increases the rate at which the glyphosate acid and ammonia react to form ammonium glyphosate and/or (ii) reduces the flow resistance of the reaction mass as it is being conveyed to the product discharge region of the reactor.

The present invention is further directed to a process for preparing a dry granular herbicidal composition, comprising continuously feeding (i) particulate glyphosate acid, (ii) ammonia, (iii) adjuvant, and (iii) water to form a reaction mass in which ammonium glyphosate is formed, wherein the amount of water fed is about 10% to about 25% by weight of all of the glyphosate acid, ammonia, adjuvant and water added to the reactor. The water content of the reaction mass is reduced to form an ammonium glyphosate paste using the heat of reaction of the glyphosate acid and ammonia to cause the evaporation of water. The reaction mass is continuously conveyed to the product discharge region of the reactor. If the ammonium glyphosate paste has a moisture content greater than about 15% by weight, heat and/or vacuum may be applied to reduce the moisture content of the composition to from about 2% to about 15% by weight. One or more adjuvant(s) in a weight ratio of total adjuvant to ammonium glyphosate of about 1:20 to about 1:2 are added to the ammonium glyphosate paste to form an extrudable ammonium glyphosate mixture. The extrudable ammonium glyphosate mixture is continuously fed to an extruder having a screen through which the ammonium glyphosate is extruded to form extrudate strands that break to form moist coherent granules. As part of the process, the adjuvant: (i) increases the rate at which the glyphosate acid and ammonia react to form ammonium glyphosate; (ii) reduces the flow resistance of the reaction mass as it is being conveyed to the product discharge region of the reactor; and/or, (iii) reduces the flow resistance of the extrudable ammonium glyphosate mixture. The granules may then be dried to produce the dry granular composition and/or further processed to classifying the granules to remove or recycle granules, fragments of granules and aggregates of granules that are outside a desired size range.

DETAILED DESCRIPTION OF THE INVENTION

In accordance with the present invention, a process has been discovered whereby particulate glyphosate acid ammonia, in the form of either anhydrous ammonia or aqueous ammonia, water and adjuvant are added to a reactor to form a reaction mass with the amount of water added being about 10% to about 25% by weight of the amount of the glyphosate acid, ammonia, water and adjuvant combined to form the reaction mass. Advantageously, the heat of reaction of glyphosate acid and ammonia causes water to evaporate, resulting in the formation of an ammonium glyphosate paste.

Surprisingly, it has been discovered that the addition of an adjuvant to the reaction mass increases the rate of formation of ammonium glyphosate paste, reduces the flow resistance of ammonium glyphosate paste or both, thereby providing a process having improved throughput and resulting in a "downstream processable" ammonium glyphosate paste having a moisture content of about 2% to about 20% by weight. The term "downstream processable", as used herein, means that the ammonium glyphosate paste is readily capable, upon further reduction in moisture content, if necessary, to about 2% to about 15% by weight of being further processed by extrusion granulation with an adjuvant to form a dry granular herbicidal composition having a weight ratio of adjuvant to ammonium glyphosate of from about 1:20 to about 1:2, preferably from about 1:9 to about 1:2. Thus, if a granular product is desired, the ammonium glyphosate paste may be mixed with additional adjuvant to form an extrudable ammonium glyphosate mixture which may then be extruded to form a granular formulation of ammonium glyphosate having a high concentration of adjuvant.

Although various steps in the process may be performed as either a batch process or a continuous process, it is preferred that some or all of the process steps are performed continuously. In particular, it is preferred that the reaction of glyphosate acid and ammonia be carried out in a continuous reactor capable of both mixing the reaction components and conveying the reaction mass to the discharge of the reactor.

I. Formation of Ammonium Glyphosate Paste

Figure 1:
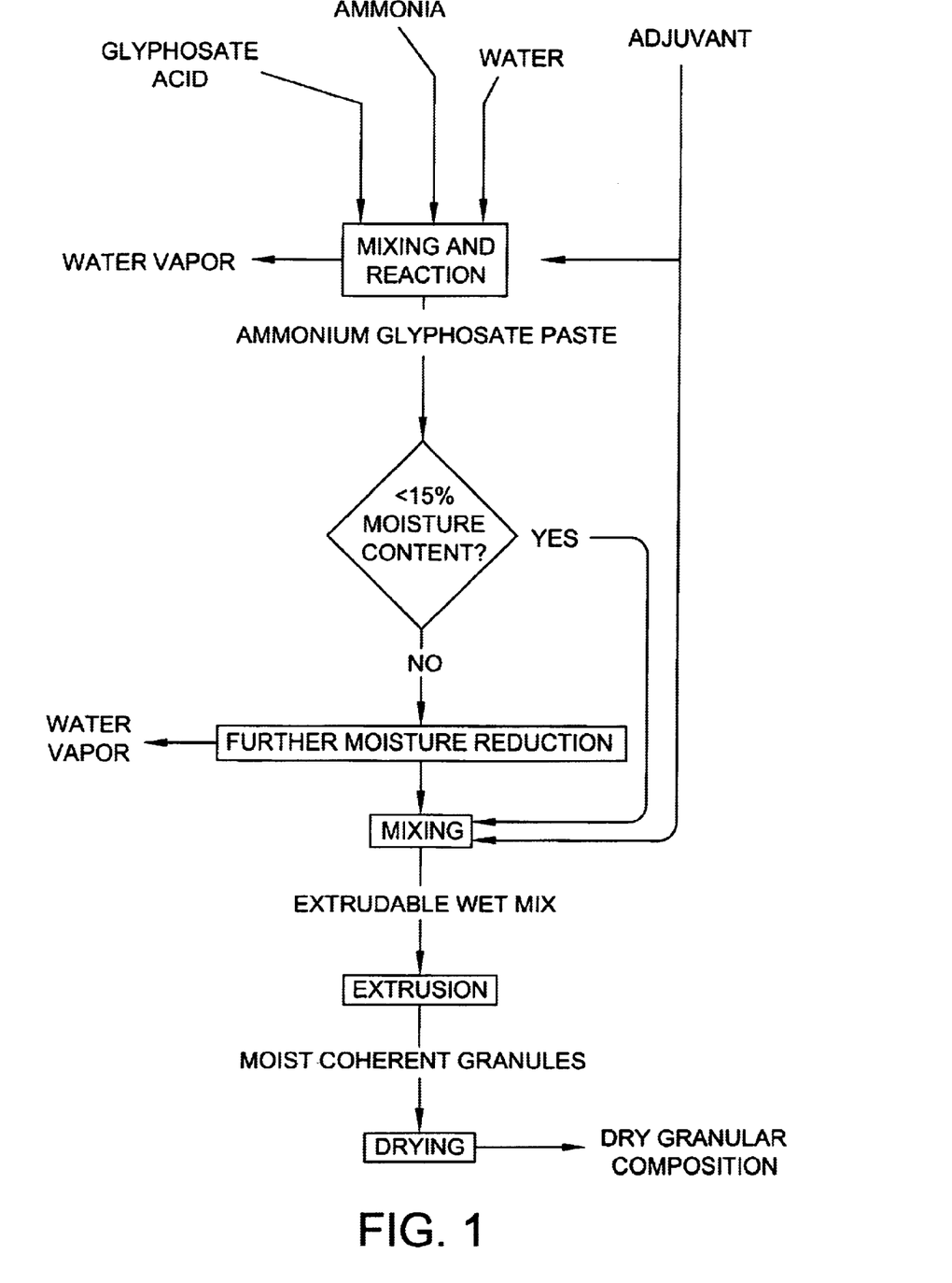
FIG. 1 shows a process flow diagram of a process of the invention for preparing a dry granular herbicidal composition.

Referring to FIG. 1, the process of the present invention is performed by feeding particulate glyphosate acid, ammonia, water and adjuvant to a reactor and mixing the reaction components to form a reaction mass wherein the ammonia reacts with the glyphosate acid to form a downstream processable ammonium glyphosate product. The reactor may be any apparatus capable of mixing solid and liquid materials to produce a paste or comparable composition such as, for example, food mixers, planetary mixers, ribbon blenders or kneaders.

In one embodiment, the reactor comprises a rotatable shaft having one or more screw elements coaxial with the shaft and bearing a plurality of radially disposed pins and/or paddles. Upon rotation of the shaft, the screw elements of such an assembly cause bulk movement of ammonium glyphosate in a direction parallel to the shaft, while simultaneously the pins and/or paddles constantly mix the ammonium glyphosate and create a large gas-solid interface. More than one of such shafts can be present, disposed parallel to one another and rotatable in the same direction or in opposite directions.

Preferably the reaction components are mixed and the ammonia and glyphosate acid react in a reactor having a substantially enclosed chamber having at an input end an aperture suitable for introduction of the particulate glyphosate acid, having at an output end an aperture suitable for discharge of the ammonium glyphosate composition, and having between the input and output ends one or more ports suitable for introduction of ammonia and water. Optionally, additional ports may be present near the output end for exhaust of water vapor and, if necessary, excess ammonia.

In one embodiment, the mixing apparatus is a continuous processor comprising an elongated chamber having one or more, preferably one or two, rotatably disposed shafts as described above, each on an axis parallel to the elongated dimension of the chamber. Operation of the apparatus by rotation of the shafts effects: (i) feeding of the glyphosate acid into the chamber through the aperture at the input end; (ii) mixing of the ingredients to form a reaction mass; (iii) transport of the reaction mass and the resulting ammonium glyphosate composition towards the output end of the chamber; and, (iv) discharge of the ammonium glyphosate product from the aperture at the output end. Water, adjuvant and ammonia may be injected through ports located between the input and output ends. Preferably, water and adjuvant are injected at or near the input end while the ammonia is preferably injected through one or more injection ports with each port being a sufficient distance from the input end to permit thorough mixing of the glyphosate acid, water and adjuvant prior to substantial exposure of the glyphosate acid with the ammonia. In one embodiment, the water and adjuvant are pre-mixed with the glyphosate acid prior to feeding the glyphosate acid into the reaction chamber, thus enabling the ammonia to be injected through one or more ports located at any location within the reaction chamber. Optionally one or more ports for venting water vapor and/or excess ammonia can be present between the ammonia injection port and the output end; however it is generally preferred that such venting occur only at the output end itself, through the discharge aperture for the ammonium glyphosate composition.

The type of apparatus just described, namely a continuous single- or twin-shaft mixer/kneader or solids processor, has been found particularly suitable when anhydrous ammonia is used, either in the gaseous or liquid state. When ammonia is injected at some distance from the input end, the atmosphere within the chamber in the vicinity of the ammonia injection port becomes rich in ammonia, and the large gas-solid interface ensures rapid and efficient reaction of the ammonia with the glyphosate acid. Rapid consumption of the ammonia in the reaction leads to a rather steep declining concentration gradient of ammonia in the internal atmosphere of the chamber, towards both the input and the output end.

If the glyphosate acid is fed in the form of wet cake and no additional water, or only a small amount of additional water is required, the degree of mixing needed before contact with the ammonia is minimal. In this situation, the ammonia injection port can, if desired, be located close to the input end of the chamber. Back-leakage of ammonia gas from the input end can be substantially prevented by arranging that screw elements on the shafts draw wet cake uninterruptedly into the chamber so that no air continuum is permitted to form between the outside and inside of the chamber at the input end. Thus, in an especially preferred process: (i) glyphosate acid in the form of wet cake is pre-mixed with adjuvant and fed uninterruptedly by screw elements disposed in the aperture at the input end of the chamber in such a way that no air continuum forms that would permit back-leakage of ammonia at the input end; (ii) the shaft rotation speed is such that residence time of the reaction mass in the chamber is sufficient to permit completion of the reaction forming the ammonium glyphosate; and, (iii) anhydrous ammonia is injected through a port located at a distance from the output end sufficient to result in substantially no venting of ammonia from the aperture at the output end. Even where the apparatus is designed for operation with close to zero emission of ammonia, it may be desirable to nevertheless treat the vented gases through a scrubber or equivalent device before release to the environment.

With the information presented herein, one of skill in the art will find it straightforward by routine testing to establish, for any particular apparatus of the type just described, a suitable shaft rotation speed (affecting glyphosate acid feed rate as well as residence time in the chamber), water feed rate, adjuvant feed rate and ammonia injection point (ammonia injection rate being tied to glyphosate acid feed rate) to operate the process of the present invention efficiently with minimal venting of ammonia. Where the apparatus has replaceable screw elements and pin and/or paddle elements on the shafts, the skilled person will also readily be able, by routine testing, to identify an optimum configuration of such elements. Equipment suitable for carrying out the present invention, i.e. continuous single-or twin-shaft mixers/kneaders or solids processors, are commercially available, for example, from Buhler Limited (Uzwil, Switzerland), Readco Manufacturing Inc. (York, Pa.) and Werner and Pflieder Corporation (Ramsey, N.J.), and are available in various sizes (for example, 5 cm, 13 cm, 20 cm, 25 cm, 38 cm, 62 cm, 93 cm, 125 cm and 175 cm) depending on the type of equipment selected and the desired throughput.

a. Adjuvant Addition to the Reaction Mass

Surprisingly, it has been discovered that the addition of an adjuvant to the reaction mixture can increase the rate of formation of the ammonium glyphosate paste. For example, the rate of formation of ammonium glyphosate in a reaction mixture comprising adjuvant, ammonia, glyphosate acid and water may be at least about 10%, at least about 30%, at least about 50%, at least about 100%, and even as much as about 150%, or more, greater than the reaction rate for a reaction mixture which is otherwise identical except for the absence of adjuvant under the same or substantially similar reaction conditions. In more absolute terms, the rate of formation of ammonium glyphosate is at least about 0.02, more preferably at least about 0.05, still more preferably at least about 0.075, still more preferably at least about 0.1, still more preferably at least about 0.2, still more preferably at least about 0.3, still more preferably at least about 0.4, still more preferably at least about 0.5, still more preferably at least about 0.75, still more preferably at least about 1.0, still more preferably at least about 1.25 gram-moles/minute-liter of reactor volume. In general, reaction rates tend to decrease with increasing reactor volume; thus, for example, a continuous reactor comprising an elongated 15 inch (about 38 cm) diameter chamber having a reactor volume of 378 liters may readily be operated to form at least about 0.4, gram-moles/minute of ammonium glyphosate, whereas reactors having smaller volumes such as a continuous reactor comprising an elongated 5 inch (about 7.5 cm) diameter chamber having a reactor volume of 14 liters may readily be operated to form at least about 0.75 gram-moles/minute of ammonium glyphosate. In one embodiment, therefore, the reaction vessel has a volume of at least about 1 liter and the rate of formation of ammonium glyphosate is at least about 1, more preferably at least about 1.5, still more preferably at least about 2, still more preferably at least about 2.5, and most preferably at least about 3.0 gram-moles/minute-liter of reactor volume. In another embodiment, the reaction vessel has a volume of at least about 10 liters and the rate of formation of ammonium glyphosate is at least about 0.5, more preferably at least about 1.0, still more preferably at least about 1.5, and still more preferably at least about 2 gram-moles/minute-liter of reactor volume. In another embodiment, the reaction vessel has a volume of at least about 15 liters and the rate of formation of ammonium glyphosate is at least about 0.5, more preferably at least about 1.0, and still more preferably at least about 1.5 gram-moles/minute-liter of reactor volume. In another embodiment, the reaction vessel has a volume of at least about 50 liters and the rate of formation of ammonium glyphosate is at least about 0.25, more preferably at least about 0.5, more preferably at least about 1.0, and still more preferably at least about 1.5 gram-moles/minute-liter of reactor volume. In another embodiment, the reaction vessel has a volume of at least about 100 liters and the rate of formation of ammonium glyphosate is at least about 0.25, more preferably at least about 0.5, more preferably at least about 1.0, and still more preferably at least about 1.25 gram-moles/minute-liter of reactor volume. In another embodiment, the reaction vessel has a volume of at least about 200 liters and the rate of formation of ammonium glyphosate is at least about 0.25, more preferably at least about 0.5, more preferably at least about 0.75, and still more preferably at least about 1.0 gram-moles/minute-liter of reactor volume. In another embodiment, the reaction vessel has a volume of at least about 300 liters and the rate of formation of ammonium glyphosate is at least about 0.25, more preferably at least about 0.5, more preferably at least about 0.75, and still more preferably at least about 1.0 gram-moles/minute-liter of reactor volume. In another embodiment, the reaction vessel has a volume of at least about 500 liters and the rate of formation of ammonium glyphosate is at least about 0.25, more preferably at least about 0.5, more preferably at least about 0.75, and still more preferably at least about 1.0 gram-moles/minute-liter of reactor volume.

In addition to increasing the rate of formation of ammonium glyphosate, inclusion of one or more adjuvant(s) in the reaction mixture has been found to provide other benefits. For example, as stated earlier, addition of an adjuvant to the reaction mass may reduce the flow resistance of the reaction mass. Accordingly, the reactor power consumption required to convey the reaction mass may be significantly reduced (e.g., 5%, 10%, 20% or even more depending upon adjuvant selected and the amount added to the reaction mass).

The adjuvant may be added to the reactor in various amounts, depending upon the adjuvant and the desired composition and properties of the final product. For example, the weight ratio of adjuvant to glyphosate acid added to a reaction mixture comprising ammonia, glyphosate acid and water may be at least about 1:250, and will typically be at least about 1:100, respectively. In some embodiments, the weight ratio of adjuvant to glyphosate acid added to the reaction mixture may be even greater with the weight ratio of adjuvant to glyphosate acid being at least about 1:75, at least about 1:50, at least about 1:25, at least about 1:10, at least about 1:5 or even about 1:2, respectively. In general, however, the weight ratio of adjuvant to glyphosate acid added to the reaction mixture will be less than about 1:2, respectively, with weight ratios of about 1:10 to about 1:250, about 1:25 to about 1:150, or even about 1:50 to about 1:100, respectively, being typical.

The adjuvant component of the reaction mixture may be a single adjuvant or it may comprise two or more adjuvant materials. Where two or more adjuvant materials are used, they may be added separately to the reaction mixture or they may first blended together and the blend may then be added to the reaction mixture. Other materials, including water and/or glycols, can optionally be admixed with the adjuvant or adjuvants prior to addition to the reaction mixture.

In general, the adjuvant added to the reaction mixture may be a nonionic surfactant, cationic surfactant, anionic surfactant, amphoteric surfactant, silicone surfactant, fluorocarbon surfactant or lubricant. Exemplary nonionic surfactants include alkylpolyglucosides; glycerol esters such as glyceryl monolaurate, and ethyoxylated glyceryl monococoate; ethoxylated castor oil; ethoxylated reduced sugar esters such as polyoxyethylene sorbitol monolaurate; esters of other polyhydric alcohols such as sorbitan monolaurate and sucrose monostearate; ethoxylated amides such as polyoxyethylene cocoamide; ethoxylated esters such as monolaurate of polyethylene glycol 1000 and dilaurate of polyethylene glycol 6000; ethoxylated alkyl or arylphenols such as nonylphenol ethoxylate, octylphenol ethoxylates, dodecylphenol ethoxylates, dinonylphenol ethoxylates and tristyrylphenol ethoxylates; alcohol ethoxylates such as fatty alcohol ethoxylates (e.g., oleyl alcohol ethoxylate), tridecylalcohol ethoxylates and other alcohol ethoxylates such as neodols and oxoalcohol ethoxylates; and ethylene oxide/propylene oxide copolymers such as pluronic type, tetronic type, or tergitol XH type. Exemplary cationic surfactants include alkylamine ethoxylates (including etheramines and diamines) such as tallowamine ethoxylate, cocoamine ethoxylate, etheramine ethoxylate, -tallow ethylenediamine ethoxylate and amidoamine ethoxylates; alkylamine quaternary amines such as alkoxylated quaternary amines (e.g., ethoxylated quaternary amines or propoxylated quaternary amines); alkylamine acetates such as tallowamine acetate or octylamine acetate; and amine oxides such as ethoxylated amine oxides (e.g., N,N-bis(2-hydroxyethyl)cocoamine-oxide), nonethoxylated amine oxides (e.g., cethyldimethylamine-oxide) and amidoamine oxides. Exemplary anionic surfactants include fatty soaps such as ammonium tallowate and sodium stearate; alkyl sulfates such as sodium $C_{8-10}$ alcohol sulfate, sodium oleyl sulfate, and sodium lauryl sulfate; sulfated oils such as sulfated castor oil; ether sulfates such as sodium lauryl ether sulfate, ammonium lauryl ether sulfate, and ammonium nonylphenol ether sulfate; sulfonates such as petroleum sulfonates, alkylbenzene sulfonates (e.g., sodium (linear) dodecylbenzene sulfonat or sodium (branched) dodecylbenzene sulfonate), alkylnapthalene sulfonates (e.g., sodium dibutylnapthalene sulfonate), alkyl sulfonates (e.g., alpha olefin sulfonates), sulfosucinnates such as dialkylsulfosuccinates (e.g., sodium dioctylsulfosuccinate) and monoalkylsulfosuccinatea and succinamides (e.g., disodium laurylsulfosuccinate and disodium N-alkylsulfosuccinamate); sulfonated amides such as sodium N-methyl N-coco taurate; isethionates such as sodium cocoyl isethionate; sarcosinates such as N-lauroyl sarcosine; and phosphates such as alkylether ethoxylate phosphates and alkylarylether ethoxyated phosphates. Exemplary amphoteric surfactants include betaines such as simple betaines (e.g., cocodimethylbetaine), sulfobetaines, amidobetaines, and cocoamidosulfobetaines; imidazolinium compounds such as disodium lauroamphodiacetate, sodium cocoamphoacetate, sodium cocoamphopropionate, disodium cocoaminodipropionate, and sodium cocoamphohydoxypropyl sulfonate; and other amphoteric surfactants such as N-alkyl, N,-bis(2-hydroxyethyl)glycine and alkylaminedipropionates. Exemplary lubricants include fatty acids such as oleic acid; silicon oils such as polydimethylsiloxane; fatty esters such as corn oil, sugars and reduced sugars. In a preferred embodiment, at least one adjuvant added to the reaction mixture is cationic, amphoteric or selected from the class of surfactants known as alkyl polyglycosides (APGs) and polyoxyethylene $C_{16-22}$ alkylethers (each of which is nonionic). Polyoxyethylene derivatives of such cationic and amphoteric surfactants are particularly preferred. The term "alkyl" is used in the present context to denote one or more linear or branched, saturated or unsaturated hydrocarbyl chains having, unless otherwise specified, about 8 to about 22 carbon atoms.

The adjuvant or adjuvant blend is preferably added in a liquid state. Solid adjuvant can be added in the solid state or alternatively can be heated to a temperature above their melting point and added in the liquid state. Solid adjuvant may also be added either as an aqueous slurry, or if the solubility of the adjuvant is sufficiently high may be added as a solution. Liquid adjuvant may also be heated to improve the flow characteristics of the adjuvant.

b. Glyphosate Acid Addition

Particulate glyphosate acid may be added to the reactor either in dry powder or a wet cake form. Although not critical to the present invention, preliminary studies indicate that glyphosate acid particles having a nominal diameter in excess of about 400 μm or even about 300 μm may adversely affect the rate at which the reaction of particulate glyphosate acid with ammonia occurs. Preferably, therefore, the particulate glyphosate acid has a particle size distribution such that at least about 80% of the particles have a nominal diameter of less than about 400 μm in diameter and more preferably less than about 300 μm. More preferably, the glyphosate acid has a particle size distribution such that at least about 90% of a nominal diameter of less than about 400 μm in diameter and more preferably less than about 300 μm. In a particularly preferred embodiment, the particle size distribution is such that the median nominal diameter is from about 30 μm to about 230 μm, more preferably from about 50 μm to about 150 μm, and still more preferably from about 75 μm to about 125 μm. However, it should be noted that the particle size distribution may vary outside these ranges without departing from the scope of the present invention.

Preferably, the particulate glyphosate acid is added in the form of a wet cake having a moisture content of less than about 18%, more preferably from about 5% to about 15%, more preferably from about 8% to about 15%, and more preferably from about 11% to about 13% by weight. If the glyphosate acid is supplied in the form of wet cake, it may be necessary to feed the glyphosate acid using a feeder, as described hereinafter, in order to maintain a constant feed rate. Glyphosate acid wet cake is a somewhat cohesive material that typically does not flow freely without the application of external force. Even when agitated, the wet cake tends to form "bridges" in static zones within the feed vessel where the wet cake is not in motion. Over time, these bridges can grow to the point that no wet cake flows from the feed vessel, resulting in an excess amount of ammonia in the downstream reaction step. When the reaction is carried out continuously, it is preferred that the glyphosate acid wet cake be fed using equipment that reliably maintains a constant feed rate and that is not susceptible to bridging.

Figure 2:
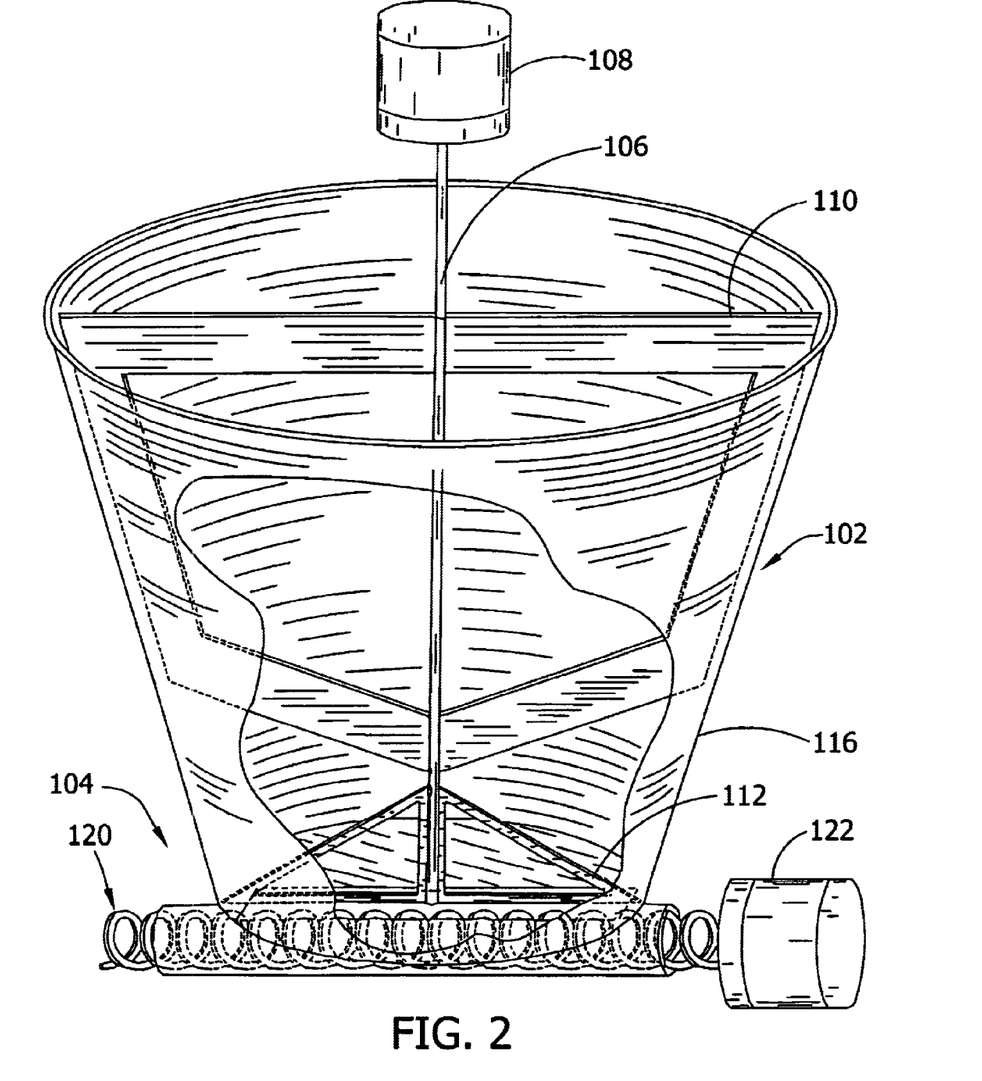
FIGS. 2 through 4 show a number of views of a gravimetric feeder suitable for supplying glyphosate acid wet cake at a constant feed rate in the process of the invention.

FIG. 2 depicts a suitable feeding apparatus that is designed to minimize the amount of bridging. The apparatus includes an upper feeder 102 and a lower feeder 104. The upperfeeder includes a feed hopper 116 equipped with an agitator 106 driven by a motor 108.

The agitator includes upper blades 110 and lower blades 112. The upper blades are preferably open paddles shaped so as to fit closely within the walls of the hopper. Lower blades 112 are placed so as to maintain a minimum clearance, preferably less than about 1.6 mm from the top of the screw in the lower feeder so as to prevent accumulation of wet cake on the bottom plate. Feeders that employ this type of agitator design typically provide about 6.5 mm clearance between the blade edges and the bottom plate. As shown more clearly in FIGS. 3 and 4, bottom plate 114 is formed with an integral trough 118 that forms the housing of lower feeder 104. If the clearance is too great between the blades and the bottom plate, bridges of wet cake may form across the top of this trough, impeding or stopping the flow of wet cake to the lower feeder. Preferably, therefore, the clearance is less than about 6.5 mm to reduce the tendency of glyphosate wet cake to accumulate on the plate. It should be noted that the agitator speed may also affect the performance of the feeder. That is, if the agitator rotates too quickly, it may force material into the lower feed unit faster than the screw can transport the wet cake into the reaction apparatus. If the agitation speed is too low, the agitator will not break up the bridges forming in the hopper. The optimum agitator speed for a given feeder design may be readily determined by routine experimentation to ensure that the feed rate is not adversely affected and that the formation of bridges is sufficiently suppressed.

Figure 3:
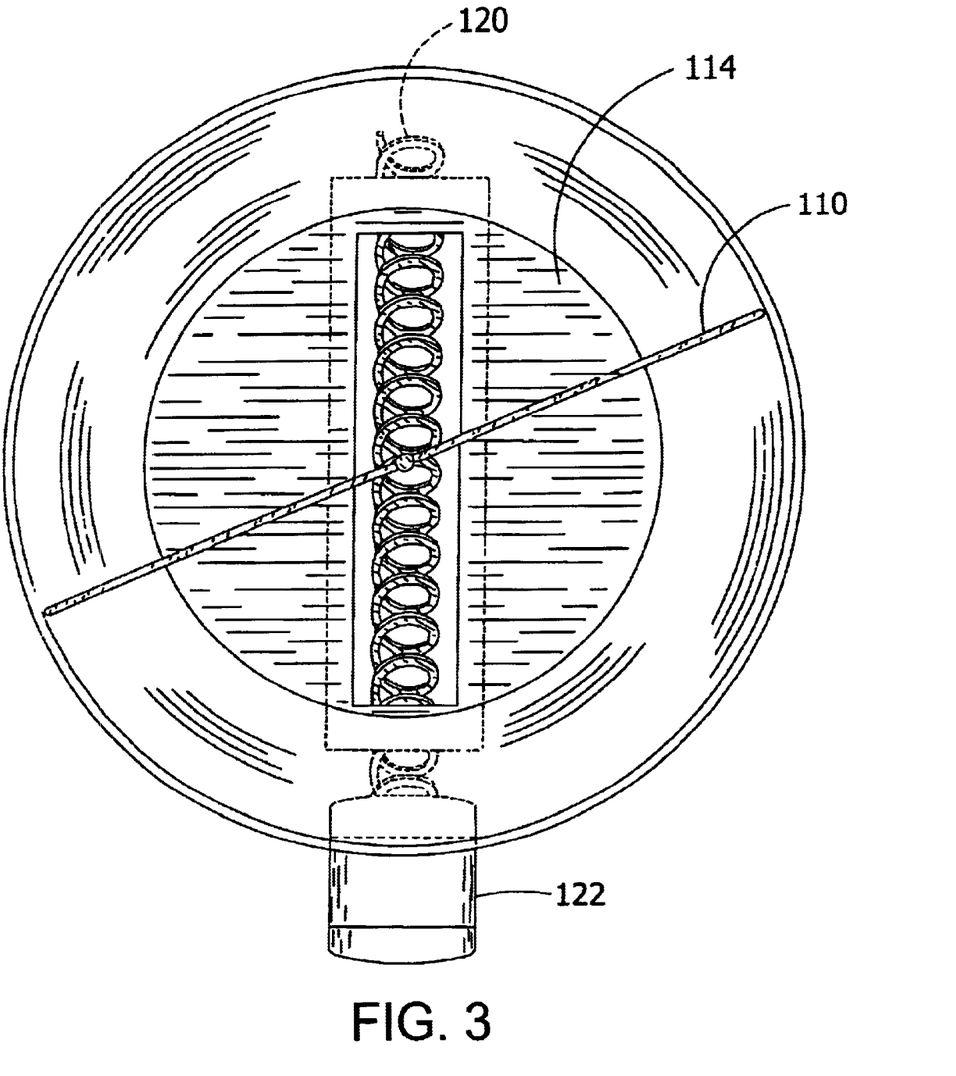
Figure 4:
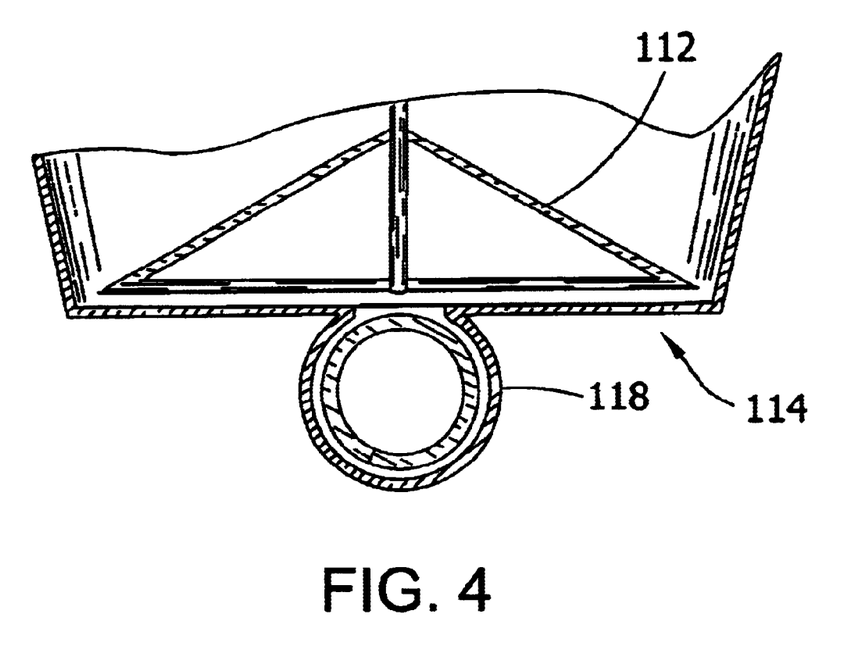

Lower feed unit 104 is preferably a conveyor capable of discharging material having a moisture content sufficient to cause bridging from the upper feeder 102 to the reactor. Preferably, the conveyor is a screw feeder comprising a single-helix, open-spiral auger 120 as shown in FIG. 3.

While the glyphosate acid is preferably fed continuously to the process using equipment as described above, any equipment that reliably maintains a constant feed rate of moist glyphosate acid may be used without departing from the scope of the present invention. Such equipment is commercially available, for example, from Merrick Industries (Lynn Haven, Fla.).

c. Ammonia Addition

Ammonia is preferably fed to the reactor at a rate sufficient to provide approximately a stoichiometric amount required to react with the glyphosate acid being fed to the reactor to form monoammonium glyphosate. Accordingly, the molar ratio of ammonia to glyphosate acid added to the reactor is about 1 mole of ammonia per mole of glyphosate acid. An ammonia addition rate of less than about 1 mole of ammonia per mole of glyphosate acid may result in a portion of the glyphosate acid remaining un-reacted. However, it is generally acceptable provided the portion of un-reacted glyphosate acid is relatively small, for example less than about 20%, resulting in the presence of at least about 4 moles of ammonium glyphosate per mole of unneutralized glyphosate acid in the reaction product, without departing from the scope of the present invention. An ammonia addition rate of greater than about 1 mole of ammonia per mole may result in the off gassing of ammonia increasing the raw material cost and the cost of environmental controls. In addition, an ammonia addition rate of greater than about 1 mole of ammonia per mole of glyphosate acid may result in a portion of the glyphosate acid reacting to form diammonium glyphosate. The diammonium salt is more hygroscopic than the monoammonium salt and therefore less desirable. Preferably, the molar ratio of ammonia to glyphosate acid added to the reactor is from about 0.8 to about 1.25, more preferably from about 0.9 to about 1.1 and still more preferably from about 0.95 to about 1.05 moles of ammonia added per mole of glyphosate acid added.

The ammonia may be fed to the reactor as aqueous ammonia ($NH_4OH$), liquid anhydrous ammonia, gaseous anhydrous ammonia or combinations thereof through one or more input ports. Aqueous ammonia contributes additional water to the reactor thereby increasing the total amount of water fed to the reactor as further discussed below. Anhydrous ammonia, whether added in liquid or gaseous form, does not affect the total water balance. However, if fed in the liquid form, part or all of the liquid anhydrous ammonia may be converted to gaseous anhydrous ammonia upon entering the reaction vessel. The liquid anhydrous ammonia absorbs the heat of vaporization required to convert the liquid ammonia to gaseous ammonia from the reaction mass thereby reducing the amount of heat that would otherwise need to be dissipated by other means, such as evaporation of water from the reaction mass or an external cooling system such as a cold water jacket. Accordingly, the ammonia is preferably fed to the reactor as anhydrous ammonia in the liquid form.

Whether the anhydrous ammonia is added in liquid form or gaseous form, at least some amount of gaseous anhydrous ammonia may subsequently exist in the reactor. Preferably, therefore, the reactor is designed to create and maintain a large interfacial area between the reaction mass and the internal atmosphere of the reactor vessel (i.e., the reactor mixes the reaction components such that a significant volume of gas is entrained in the reaction mass.) This interfacial area, herein referred to as the gas-paste interface, may affect the efficiency with which the glyphosate acid reacts with ammonia gas present in the internal atmosphere.

d. Water Addition

The total amount of water fed to the reactor is preferably from about 10% to about 25% and more preferably from about 13% to about 18% by weight of all of the glyphosate acid, ammonia, water and adjuvant added to the reaction vessel. Within this range, the amount of water present in the initial reaction mass is not narrowly critical. The precise amount of water for a particular apparatus and set of reaction conditions may be readily determined by one of skill in the art.

In general, the amount of water fed to the reactor is preferably sufficient to contribute usefully to dissipation of heat by evaporative cooling. That is, the evaporation of water from the reaction mass dissipates some of the heat generated in the reaction. While the reaction may be carried out at temperatures as low as ambient temperatures, the temperature of the reaction mass typically increases rapidly due to the exothermic nature of the reaction. The temperature at which the reaction is carried out is typically from about 70° C. to about 105° C. and is more preferably about 100° C. Typically, the reaction mass is cooled to prevent the reaction from overheating; the evaporation of water from the reaction mass reduces the amount of heat that would otherwise need to be removed by other means. Advantageously, the evaporation of water additionally reduces the amount of water that may need to be removed in a subsequent step if a lower water content material is desired.

Although some reduction in moisture concentration is desirable; it is also desirable to maintain a sufficient concentration to sustain the homogeneity of the reaction mass to ensure the completion of the reaction. That is, the evaporation of some of the water in the reaction mass also reduces the moisture content, thus affecting the flow characteristics of the reaction mass. Accordingly, the water is preferably fed to the reactor at a rate sufficient to provide not only the evaporative cooling effect as described above, but also to ensure the reaction mass may be readily homogenized with the degree of energy available in the mixing system used in the reactor, so that the acid-base reaction proceeds smoothly and completely producing a downstream processable paste. In some types of high-energy mixing or kneading equipment having an effective conductive cooling system in the form, for example, of a water jacket, a relatively stiff paste having relatively low moisture content is acceptable, whereas in lower-energy equipment or equipment having a less effective conductive cooling system it can be desirable to form a wetter, more fluid paste.

The proportion of water that is added as part of the moist glyphosate acid, ammonia or adjuvant may vary without departing from the scope of the present invention provided the total amount of water added is consistent with the above stated range. For example, where 100 parts by weight of glyphosate acid are mixed with 10 parts by weight of ammonia (both expressed on a water-free basis) and no other ingredients except water are added in the reaction step, a suitable amount of water is about 12 to about 37 parts by weight. As described above, part or all of this water can be present in the glyphosate acid or ammonia composition added. For example, if 10 parts by weight ammonia in the form of aqueous ammonia (29% by weight ammonia, 71% by weight water) are added to 100 parts by weight glyphosate acid in the form of wet cake having 10% moisture content, the total amount of water present in these ingredients is about 35.6 parts by weight and the maximum amount of additional water to be added is about 1.4 parts by weight. In general, no addition of water is needed in such a situation. However, if 10 parts by weight anhydrous ammonia are added to 100 parts by weight glyphosate acid in the form of wet cake having 12% moisture content, the total amount of water present in these ingredients is only about 13.6 parts by weight, and up to about 23.4 parts by weight of additional water can be added.

Typically the evaporation of water results in a decrease of about 1 to about 15 and more typically from about 1 to about 10 percentage points in the moisture content of the reaction mass during reaction step such that the ammonium glyphosate paste discharged from the reactor may have a moisture content of from about 0.1% to about 20%. Preferably, the ammonium glyphosate paste has a moisture content of from about 2% to about 20%, more preferably from about 2% to about 15%, still more preferably from about 2% to about 10%, still more preferably from about 2% to about 5% and most preferably from about 3% to about 5% by weight. It should be noted that a substantial amount of water may continue to evaporate from the reaction mass during cooling; thus, the water content in the reaction mass is preferably determined after the composition has been allowed to cool to about 50° C. to about 70° C. The moisture content can be measured using any means known in the art for determining such a composition; devices capable of measuring the moisture content are commercially available, for example, from Denver Instrument Company (Arvada, Colo.).

If the moisture content of the ammonium glyphosate paste is greater than about 15% by weight, additional heat can added to the reaction to increase water evaporation; additionally or alternatively, further reduction in moisture content of the composition can be effected by application of heat and/or vacuum to the composition after completion of the reaction step. Any moisture reduction or partial drying method known in the art can be used.

To avoid the necessity for application of heat and/or vacuum to drive off further water, it is preferred that the process conditions are such that the ammonium glyphosate paste has a moisture content of no greater than about 15% by weight. More precisely, it is preferable to add no more water at the beginning of the process than is necessary to provide a suitable composition consistency and sufficient evaporative cooling, and to result in a downstream processable ammonium glyphosate paste having a moisture content of from about 2% to about 15%, still more preferably from about 2% to about 10%, still more preferably from about 2% to about 5% and most preferably from about 3% to about 5% by weight. Preferably, therefore, the ammonia is added as anhydrous ammonia and the amount of water introduced, including moisture associated with the glyphosate acid, is preferably less than about 18% and more preferably less than about 15% by weight of all of the glyphosate acid, ammonia, water and adjuvant added.

The ammonium glyphosate paste produced by the process described in detail above can be packaged as a concentrate herbicidal composition, either as produced or dried, for example by drum drying to form solid flakes. In addition, depending on the amount of adjuvant added and the moisture content of the ammonium glyphosate paste, the paste may solidify upon cooling to form mixture that "crumbles" to the touch.

II. Granulation Process

Surprisingly, the ammonium glyphosate paste of the present invention has been found to be particularly suitable as an intermediate in preparation of a dry granular herbicidal composition as more particularly described below. What is especially surprising is that the ammonium glyphosate in the downstream processable paste form generated herein has been found to have the required absorbency and/or adsorbency properties to enable efficient formulation as a dry granular herbicidal composition with adjuvant at up to about 25% by weight of the finished formulation, by a process of extrusion granulation.

In another embodiment of the present invention, therefore, the ammonium glyphosate paste is further processed to form dry ammonium glyphosate granules. According to this embodiment, the additional adjuvant is added to the ammonium glyphosate paste and mixed until a homogeneous wet mix, preferably having a dough-like consistency, herein referred to as an extrudable ammonium glyphosate mixture is formed. Preferably, the adjuvant is a surfactant capable of enhancing the herbicidal efficacy of the finished product. In a particularly preferred embodiment the adjuvant(s) comprise one or more cationic surfactants. Depending upon the amount of adjuvant added to the reaction mixture, one or more adjuvant(s) (separately or as a blend, if more than one is used) may be combined with the ammonium glyphosate paste. In one embodiment, additional quantities of the adjuvant(s) added to the reaction mass are also combined with the finished ammonium glyphosate paste; in another embodiment, the adjuvant(s) added to the reaction mass differ in some respect (composition or relative proportion if more than one) from the adjuvant(s) combined with the finished ammonium glyphosate paste. Typically, the amount of adjuvant added to the reaction mass will be less than the amount of adjuvant added to the finished ammonium glyphosate paste.

The weight ratio of total adjuvant to ammonium glyphosate depends, among other things, on the type of adjuvant or adjuvant used. Such a ratio will often be a compromise between, on the one hand, providing sufficient adjuvant to give a high degree of herbicidal efficacy of the finished product, and on the other hand, less that the amount of adjuvant that results in the finished granules being sticky or otherwise prone to aggregate and form lumps. The ratio of adjuvant to glyphosate acid which produces a high degree of herbicidal efficacy without producing a dry granular formulation having sticky granules may be determined as matter of routine testing by one of skill in the art. Taking into account the adjuvant added to the reaction mixture and the additional adjuvant added to the finished ammonium glyphosate paste prior to extrusion, the weight ratio of total adjuvant to ammonium glyphosate (on a dry basis) in the finished granules is generally about 1:9 to about 1:2. Typically, the weight ratio will be about 1:6 to about 1:3; where the adjuvant selected is a polyoxyethylene alkylamine, for example ethoxylated (20) tallowamine, a particularly useful weight ratio has been found to be about 1:3 to about 1:5.

Addition of adjuvant to the ammonium glyphosate paste immediately on completion of the reaction step, without permitting the composition to cool, may result in the adjuvant failing to mix intimately with the paste to form an extrudable ammonium glyphosate mixture. Although some adjuvant are more tolerant than others in this respect, it is generally preferred to add the adjuvant to ammonium glyphosate paste after the paste has cooled to a temperature of from about 25° C. to about 75° C., more preferably about 50° C. to about 70° C. and more preferably about 70° C.

In one embodiment of the present invention, the ammonium glyphosate paste and adjuvant are mixed to form an extrudable wet mix in the same vessel in which the reaction step is carried out. Preferably in such an embodiment, the ammonia and glyphosate acid react to form an ammonium glyphosate paste and the paste cools to a temperature of less than about 70° C. prior to the addition of the adjuvant to form the extrudable ammonium glyphosate mixture. That is, the glyphosate acid, ammonia, adjuvant and water enter at the input end of the reactor to form a reaction mass. The reaction mass is conveyed over some distance towards the discharger of the reactor herein referred to as the reactor zone. The ammonium glyphosate paste formed in the reactor zone is then conveyed through a cooling zone, wherein the paste is cooled from the temperature at which the reaction takes place (i.e., about 70° C. to about 105° C.) to a temperature of less than about 70° C. Finally, adjuvant is added to the cooled paste to form an extrudable ammonium glyphosate mixture and the extrudable ammonium glyphosate paste is discharged from the discharge end of the reactor. The rates at which the glyphosate acid, ammonia, adjuvant and water near the input end are similar and at which the additional adjuvant is added to the cooled ammonium glyphosate paste are controlled so that the ingredients are mixed in the desired proportions.

In another embodiment, reaction occurs in a continuous reactor as described above to form the ammonium glyphosate paste which is then fed continuously to a separate mixing apparatus, for example a continuous kneader, wherein the additional adjuvant is added to the ammonium glyphosate paste to form an extrudable ammonium glyphosate mixture. Such continuous mixing apparatus are commercially available, for example, from Fuji Paudal Ltd. (Osaka, Japan) and Readco Manufacturing Inc. (York, Pa.).

Other materials can optionally be added to either the process for producing the ammonium glyphosate paste or the process for forming the extrudable ammonium glyphosate mixture without departing from the process of the present invention. For example, a small amount of sodium sulfite can be added to inhibit nitrosamine formation. In addition, or alternatively, other ingredients which enhance the herbicidal activity i.e., inorganic salts such as ammonium sulfate, or even a second herbicidal active ingredient may be added.

The second herbicidal active ingredient, if included, can be, like glyphosate, an acid which is converted to its ammonium salt during mixing with ammonia in step (a). Illustrative examples of such herbicides are acifluorfen, asulam, benazolin, bentazon, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr. Alternatively, any of these herbicidal active ingredients can be added already neutralized and in the form of a salt.

Salts of the above herbicides are generally water-soluble and the end-product of the process is a water-soluble granular formulation. Optionally, a water-insoluble herbicidal active ingredient can be included in the mix, in which case the end-product of the process is a water-dispersible granular formulation. Water-insoluble herbicides useful in this embodiment of the invention illustratively include acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate.

The extrudable ammonium glyphosate mixture is fed to an extruder to form moist ammonium glyphosate granules. The extruder preferably has an inlet through which the extrudable ammonium glyphosate mixture is fed, and outlet comprising a screen having apertures through which the extrudable ammonium glyphosate mixture is extruded to form extrudate strands, and a conveyor for transporting the extrudable ammonium glyphosate mixture from the inlet to the outlet. The extrusion process may be carried out in any extruder apparatus known in the art, such as basket-type extruders, axial extruders, radial extruders or twin dome extruders. In a preferred embodiment, the extrusion process may be carried out using a low-pressure radial or twin-dome extruder. Such extruders are commercially available, for example, from Fuji Paudal Company Ltd. (Osaka, Japan), Readco Manufacturing Inc. (York, Pa.) and Bonnett Co. (Union Town, Ohio).

The extrudable ammonium glyphosate mixture is preferably extruded through screens having apertures preferably of diameter about 0.5 to about 2 mm, more preferably about 0.6 to about 1.5 mm. Screens with apertures having a nominal diameter within this range, for example screens with apertures having a nominal diameter of about 0.5 mm, about 0.6 mm, about 0.7 mm, about 1.0 mm, about 1.2 mm or larger are commercially available, for example, from LCI Corporation (Charlotte, N.C.). The size of the apertures is selected based on the desired size of the ammonium glyphosate granules and is not critical to the process of the present invention.

The addition of adjuvant to the reaction mass and additionally to the ammonium glyphosate paste (prior to the extrusion step, in particular) results in the formation of an extrudable ammonium glyphosate mixture which is less sticky and less abrasive to the extrusion die or screen. Accordingly, the amount of power required by the extruder may be significantly reduced (e.g., a reduction in power required of about 5%, 10%, 20% 30% or even more, depending upon adjuvant selected and the amount added to the reaction mixture). In addition, the throughput of the extruder may be significantly increased (e.g., an increase in throughput of about 5%, 10%, 25%, 50% or even more depending on the adjuvant selected and the amount added to the reaction mixture).

The extrudate emerging from the screens initially forms elongated strands which tend to break spontaneously to form short cylindrical granules. If the strands do not break readily it may be necessary to add a cutting device at the extruder head; however, if the ammonium glyphosate powder has the desired absorption and/or adsorption properties and the amount of water added is within the optimum range as described above, a cutting operation is usually not necessary.

Immediately after extrusion, the granules are moist and coherent, but are not sticky and do not agglomerate. At this point the granules can, if desired, be subjected to a rolling or tumbling action, for example in a tumbler or spheronizer, to give them a more rounded shape and to make them more uniform in size.

Finally, the moist granules may be dried to further reduce the moisture concentration if desired. Any known drying method can be used, but a preferred method is fluid bed drying. Preferably, a continuous fluid bed dryer is used with continuous inward feed from the extruder and continuous outward feed, for example to a holding vessel or packaging unit, optionally via a classifying step as indicated below. The granules are preferably dried to a moisture content below about 1%, more preferably below about 0.5%, by weight.

After drying, the granules can be packaged or held in a hopper or other storage vessel until ready for packaging, but it is generally preferred to first classify the granules, for example by sieving, to retain only those in a desired size range. This is optional step (e) of the process of the present invention. An illustrative size range to be retained is larger than 40 mesh (about 0.6 mm) and smaller than 5 mesh (about 5 mm). Over- and under-sized granules or fragments or aggregates thereof can be recycled by adding them to the wet mix prior to extrusion.

EXAMPLES

The following Examples are provided for illustrative purposes only and are not intended to limit the scope of the present invention. The Examples will permit better understanding of the invention and perception of its advantages and certain variations of execution.

Example 1

Quality Improvement

This example illustrates the difference of running the continuous reactor with and without adjuvant. The composition was prepared in a co-rotating twin screw mixer with 5″ diameter screws (manufactured by Readco Manufacturing Inc., York, Pa.). Glyphosate acid wetcake, water, and liquid anhydrous ammonia were injected into the reactor. The ammonia reacted with the glyphosate to produce a paste of ammonium glyphosate. Water vapor was flashed from the product at the exit of the mixer. A 1% solution of paste in water was approximately pH 4. Witco FloMo 1407 surfactant was mixed with the resulting paste and the mixture was extruded through a 1.0 mm die and dried in a fluid bed drier to produce a water soluble granule containing glyphosate and surfactant. When extruded, the dough formed long strands which readily formed lumps with slight pressure. After drying the product was soft.

Without stopping the above process, one weight percent of surfactant was injected into the front end of the mixer and the water addition was lowered to maintain the same moisture content of the paste as above. Power consumption quickly dropped approximately 37% with little fluctuation. A 1% solution of paste in water was approximately pH 4. Witco FloMo 1407 surfactant was added as above. The resulting mixture was extruded through a 1.0 mm die and dried in a fluid bed drier to produce a Water Soluble Granule containing glyphosate and surfactant. When extruded, the dough formed short strands which did not readily form lumps. After drying, the product had a hard crisp texture.

Example 2

Faster Reaction

This example illustrates the faster reaction achieved with surfactant addition. This example is essentially the same as Example 1 with the same inputs. After achieving equilibrium without surfactant addition, a hot stop was performed by stopping all operations simultaneously. The reactor was opened and samples were taken at selected points along the reactor. A pH was taken of the samples after dilution in water. The results indicate that all of the reaction with ammonia occurs downstream from the point of ammonia injection. Each successive sample downstream from the injection point had a higher pH indicating that the reaction was occurring all the way down the reaction chamber.

The reactor was restarted with inputs equivalent to that in the second part of example 1. After achieving equilibrium with surfactant addition, a hot stop was performed by stopping all operations simultaneously. The reactor was opened and samples were taken at the same selected points along the reactor as above. A pH was taken of the samples after dilution in water. The results indicate that all of the reaction with ammonia occurs downstream from the point of ammonia injection. The pH of each successive sample downstream from the injection point increased for the first half of the reactor and then remained constant, indicating that the reaction was complete within the first half of the reactor.

Example 3

Higher Throughput

This example illustrates the greater throughput possible with the addition of surfactant. This example is essentially the same as Example 2 with the same inputs. After achieving equilibrium without surfactant addition at the initial conditions, the reaction rate was 0.76 gram-moles/minute-liter of reaction volume. The rates of all chemical inputs were then increased 18%. A strong smell of ammonia was detected coming from the outlet, indicating that the reaction was not coming to completion, indicating that the reaction rate was less than 0.89 gram-moles/mine-liter of reaction volume. Witco FloMo 1407 surfactant was introduced at one weight percent and the water rate was left unchanged. After the surfactant was introduced, ammonia was no longer detected from the discharge, indicating that the reaction-was completed. The rate of all chemical inputs was then increased an additional 42%. Even at this production rate of 1.27 gram-moles/minute-liter of reaction of volume, product was still of good quality with no ammonia odor.

In view of the above, it will be seen that the several objects of the invention are achieved. As various changes could be made in the above-described process without departing from the scope of the invention, it is intended that all matters contained in the above description be interpreted as illustrative and not in a limiting sense. In addition, when introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

What is claimed is:

1. A process for preparing an ammonium glyphosate paste composition, comprising mixing in a reactor (i) particulate glyphosate acid, (ii) ammonia, (iii) water and (iv) adjuvant to form a reaction mass wherein the glyphosate acid and ammonia react, thereby forming an ammonium glyphosate paste composition, the total amount of water added to the reactor being from about 10% to about 25% by weight of all of the glyphosate acid, ammonia, water and adjuvant added to the reactor.

2. The process of claim 1 wherein the weight ratio of adjuvant to glyphosate acid added to the reactor is at least about 1:500.

3. The process of claim 1 wherein the weight ratio of adjuvant to glyphosate acid added to the reactor is at least about 1:250.

4. The process of claim 1 wherein the weight ratio of adjuvant to glyphosate acid added to the reactor is from about 1:100 to about 1:2.

5. The process of claim 1 wherein the weight ratio of adjuvant to glyphosate acid added to the reactor is from about 1:50 to about 1:2.

6. The process of claim 1 wherein the weight ratio of adjuvant to glyphosate acid added to the reactor is from about 1:20 to about 1:2.

7. The process of claim 1 wherein the molar ratio of ammonia to glyphosate acid added to the reactor is from about 0.8 to about 1.25.

8. The process of claim 1 wherein the molar ratio of ammonia to glyphosate acid added to the reactor is from about 0.9 to about 1.1.

9. The process of claim 1 wherein the molar ratio of ammonia to glyphosate acid added to the reactor is from about 0.95 to about 1.05.

10. The process of claim 1 wherein the total amount of water added to the reactor is from about 15% to about 18% by weight of all of the glyphosate acid, ammonia, water and adjuvant added to the reactor.

11. The process of claim 1 wherein the ammonium glyphosate paste composition has a moisture content of from about 2% to about 20% by weight.

12. The process of claim 1 wherein the ammonium glyphosate paste composition has a moisture content of from about 2% to about 15% by weight.

13. The process of claim 1 wherein the ammonium glyphosate paste composition has a moisture content of from about 2% to about 10% by weight.

14. The process of claim 1 wherein the ammonium glyphosate paste composition has a moisture content of from about 3% to about 5% by weight.

15. The process of claim 1 wherein the adjuvant is selected from the group consisting of a nonionic surfactant, cationic surfactant, anionic surfactant, amphoteric surfactant, silicone surfactant, fluorocarbon surfactant, lubricant and mixtures thereof.

16. The process of claim 15 wherein the adjuvant is a cationic surfactant.

17. The process of claim 16 wherein the cationic surfactant is selected from the group consisting of alkylamine ethoxylates, alkylamine quaternary amines, alkylamine acetates, amine oxides and mixtures thereof.

18. The process of claim 17 wherein the molar ratio of ammonia to glyphosate acid added to the reactor is from about 0.8 to about 1.25.

19. The process of claim 17 wherein the molar ratio of ammonia to glyphosate acid added to the reactor is from about 0.9 to about 1.1.

20. The process of claim 17 wherein the molar ratio of ammonia to glyphosate acid added to the reactor is from about 0.95 to about 1.05.

21. The process of claim 17 wherein the total amount of water added to reactor is from about 15% to about 18% by weight of all of the glyphosate acid, ammonia, water and adjuvant added to the reactor.

22. The process of claim 17 wherein the ammonium glyphosate paste composition has a moisture content of from about 2% to about 20% by weight by weight.

23. The process of claim 17 wherein the ammonium glyphosate paste composition has a moisture content of from about 2% to about 15% by weight.

24. The process of claim 17 wherein the ammonium glyphosate paste composition has a moisture content of from about 2% to about 10% by weight.

25. The process of claim 17 wherein the ammonium glyphosate paste composition has a moisture content of from about 3% to about 5% by weight.

26. The process of claim 1 wherein all or part of the water in the reactor is introduced as moisture associated with the glyphosate acid and/or as the water component of aqueous ammonia or adjuvant.

27. The process of claim 1 wherein the ammonia is introduced as anhydrous ammonia.

28. The process of claim 27 wherein the ammonia is introduced as liquid anhydrous ammonia.

29. The process of claim 27 wherein the water is introduced, in whole or in part as moisture associated with the glyphosate acid.

30. The process of claim 27 wherein the water is introduced, in whole or in part as moisture associated with the glyphosate acid, in an amount of about 13% to about 18% by weight of all of the glyphosate acid, ammonia, water and adjuvant added to the reactor.

31. The process of claim 30 wherein the ammonium glyphosate paste composition formed has a moisture content of from about 2% to about 10% by weight and is downstream processable without further reduction in moisture content.

32. The process of claim 30 wherein the ammonium glyphosate paste composition formed has a moisture content of from about 3% to about 5% by weight and is downstream processable without further reduction in moisture content.

33. The process of claim 27 wherein the process is a continuous process conducted in a continuous reactor comprising:

a substantially enclosed elongated chamber having (i) at an input end an aperture suitable for introduction of the particulate glyphosate acid, (ii) at an output end an aperture suitable for discharge of the ammonium glyphosate paste composition, and (iii) between the input and output end one or more ports suitable for introduction of ammonia and water; and having disposed therein one or more rotatable shafts, each on an axis parallel to the elongated dimension of the chamber, each having one or more screw elements coaxial with the shaft and bearing a plurality of radially disposed pins and/or paddles, such that rotation of the shafts effects one or more of the following: (i) feeding of the glyphosate acid into the chamber through the aperture at the input end, (ii) mixing of the glyphosate acid, ammonia, adjuvant and water to form a reaction mass having a large gas-paste interface, (iii) transport of the reaction mass and the resulting ammonium glyphosate paste composition towards the output end of the chamber, and (iv) discharge of the ammonium glyphosate paste composition from the aperture at the output end.

34. The process of claim 33 wherein the adjuvant reduces the reactor power consumption by at least about 5%.

35. The process of claim 33 wherein the adjuvant reduces the reactor power consumption by at least about 10%.

36. The process of claim 33 wherein the adjuvant reduces the reactor power consumption by at least about 20%.

37. The process of claim 33 wherein (i) glyphosate acid in the form of wet cake is fed uninterruptedly by screw elements disposed in the aperture at the input end of the chamber in such a way that no air continuum forms that would permit back-leakage of ammonia at the input end; (ii) shaft rotation speed is such that residence time of glyphosate acid in the chamber is sufficient to permit completion of the reaction forming the ammonium glyphosate paste composition; and (iii) the ammonia is injected through a port located at a distance from the output end of the chamber sufficient to result in substantially no venting of ammonia from the aperture at the output end.

38. A continuous process for preparing an ammonium glyphosate paste composition in a reactor, the process comprising continuously feeding (i) particulate glyphosate acid, (ii) ammonia, (iii) water and (vi) adjuvant to the reactor to form a reaction mass in which ammonium glyphosate is formed and heat is generated by reaction of the glyphosate acid and the ammonia, the total amount of water added to the reactor being from about 10% to about 25% by weight of all of the particulate glyphosate acid, ammonia, water and adjuvant fed to the reactor;

reducing the water content of the reaction mass to from about 2% to about 15% by weight using the heat of reaction of the glyphosate acid and the ammonia to cause the evaporation of water thereby forming the ammonium glyphosate paste composition; and conveying the ammonium glyphosate paste composition to a product discharge region of the reactor;

wherein the adjuvant (i) increases the rate at which the glyphosate acid and ammonia react to form ammonium glyphosate or (ii) reduces the flow resistance of the reaction mass and the subsequently formed ammonium glyphosate paste composition as it is being conveyed to the product discharge region of the reactor.

39. The process of claim 38 wherein the adjuvant is selected from the group consisting of a nonionic surfactant, cationic surfactant, anionic surfactant, amphoteric surfactant, silicone surfactant, fluorocarbon surfactant, lubricant and mixtures thereof.

40. The process of claim 39 wherein the adjuvant is a cationic surfactant.

41. The process of claim 40 wherein the cationic surfactant is selected from the group consisting of alkylamine ethoxylates, alkylamine quaternary amines, alkylamine acetates, amine oxides or combinations thereof.

42. The process of claim 38 wherein the rate of formation of ammonium glyphosate is at least about 0.05 gram-moles/minute-liter of reactor volume.

43. The process of claim 38 wherein the rate of formation of ammonium glyphosate is at least about 0.075 gram-moles/minute-liter of reactor volume.

44. The process of claim 38 wherein the rate of formation of ammonium glyphosate is at least about 0.1 gram-moles/minute-liter of reactor volume.

45. The process of claim 38 wherein the rate of formation of ammonium glyphosate is at least about 0.2 gram-moles/minute-liter of reactor volume.

46. The process of claim 38 wherein the rate of formation of ammonium glyphosate is at least about 0.3 gram-moles/minute-liter of reactor volume.

47. The process of claim 38 wherein the rate of formation of ammonium glyphosate is at least about 0.4 gram-moles/minute-liter of reactor volume.

48. The process of claim 38 wherein the weight ratio of adjuvant to glyphosate acid added to the reactor is at least about 1:500.

49. The process of claim 38 wherein the weight ratio of adjuvant to glyphosate acid added to the reactor is at least about 1:250.

50. The process of claim 38 wherein the weight ratio of adjuvant to glyphosate acid added to the reactor is from about 1:100 to about 1:2.

51. The process of claim 38 wherein the weight ratio of adjuvant to glyphosate acid added to the reactor is from about 1:50 to about 1:2.

52. The process of claim 38 wherein the weight ratio of adjuvant to glyphosate acid added to the reactor is from about 1:20 to about 1:2.

53. The process of claim 38 wherein the molar ratio of ammonia to glyphosate acid added to the reactor is from about 0.8 to about 1.25.

54. The process of claim 38 wherein the molar ratio of ammonia to glyphosate acid added to the reactor is from about 0.9 to about 1.1.

55. The process of claim 38 wherein the molar ratio of ammonia to glyphosate acid added to the reactor is from about 0.95 to about 1.05.

56. The process of claim 38 wherein the total amount of water added to the reactor is from about 13% to about 18% by weight of all of the glyphosate acid, ammonia, water and adjuvant added to the reactor.

57. The process of claim 38 wherein the ammonium glyphosate paste composition has a moisture content of from about 2% to about 20% by weight.

58. The process of claim 38 wherein the ammonium glyphosate paste composition has a moisture content of from about 2% to about 15% by weight.

59. The process of claim 38 wherein the ammonium glyphosate paste composition has a moisture content of from about 2% to about 10% by weight.

60. The process of claim 38 wherein the ammonium glyphosate paste composition has a moisture content of from about 3% to about 5% by weight.

61. The process of claim 38 wherein all or part of the water in the reactor is introduced as moisture associated with the glyphosate acid and/or as the water component of aqueous ammonia or adjuvant.

62. The process of claim 38 wherein the ammonia is introduced as anhydrous ammonia.

63. The process of claim 62 wherein the ammonia is introduced as liquid anhydrous ammonia.

64. The process of claim 62 wherein the water is introduced, in whole or in part as moisture associated with the glyphosate acid.

65. The process of claim 62 wherein the water is introduced, in whole or in part as moisture associated with the glyphosate acid, in an amount of about 13% to about 18% by weight of all of the glyphosate acid, ammonia, water and adjuvant added to the reactor.

66. The process of claim 62 wherein the ammonium glyphosate paste composition formed has a moisture content of from about 2% to about 15% by weight and, is downstream processable without further reduction in moisture content.

67. The process of claim 62 wherein the ammonium glyphosate paste composition formed has a moisture content of from about 3% to about 5% by weight and is downstream processable without further reduction in moisture content.

68. The process of claim 62 wherein the continuous process is conducted in a mixing apparatus comprising:
a substantially enclosed elongated chamber having (i) at an input end an aperture suitable for introduction of the particulate glyphosate acid, (ii) at an output end an aperture suitable for discharge of the ammonium glyphosate paste composition, and (iii) between the input and output ends one or more ports suitable for introduction of ammonia and water; and having disposed therein
one or more rotatable shafts, each on an axis parallel to the elongated dimension of the chamber, each having one or more screw elements coaxial with the shaft and bearing a plurality of radially disposed pins and/or paddles, such that rotation of the shafts effects one or more of the following: (i) feeding of the glyphosate acid into the chamber through the aperture at the input end, (ii) mixing of the glyphosate acid, ammonia, adjuvant and water to form a reaction mass having a large gas-paste interface, (iii) transport of the reaction mass and the resulting ammonium glyphosate paste composition towards the output end of the chamber, and (iv) discharge of the ammonium glyphosate paste composition from the aperture at the output end.

69. The process of claim 68 wherein (i) glyphosate acid in the form of wet cake is fed uninterruptedly by screw elements disposed in the aperture at the input end of the chamber in such a way that no air continuum forms that would permit back-leakage of ammonia at the input end; (ii) shaft rotation speed is such that residence time of glyphosate acid in the chamber is sufficient to permit completion of the reaction forming the ammonium glyphosate paste composition; and (iii) the ammonia is injected through a port located at a distance from the output end of the chamber sufficient to result in substantially no venting of ammonia from the aperture at the output end.

70. A continuous process for preparing an ammonium glyphosate paste composition, the process comprising:
continuously feeding (i) particulate glyphosate acid, (ii) ammonia, (iii) water and (ix) adjuvant to a continuous reactor to form a reaction mass in which ammonium glyphosate is formed and heat is generated by reaction of the glyphosate acid and the ammonia, the total amount of water added to the reactor being from about 10% to about 25% by weight of all of the particulate glyphosate acid, ammonia, water and adjuvant fed to the reactor;
reducing the water content of the reaction mass to from about 2% to about 15% by weight using the heat of reaction of the glyphosate acid and the ammonia to cause the evaporation of water and form ammonium glyphosate paste composition;
conveying the ammonium glyphosate paste composition to a product discharge region of the reactor;
adding adjuvant to the ammonium glyphosate paste composition to form an extrudable ammonium glyphosate mixture; and
continuously feeding the extrudable ammonium glyphosate mixture to an extruder having an inlet, a conveyor and an outlet with the outlet consisting essentially of a screen through which the extrudable ammonium glyphosate mixture is extruded to form extrudate strands that break or are cut to form moist coherent granules.

71. The process of claim 70 wherein the adjuvant is selected from the group consisting of a nonionic surfactant, cationic surfactant, anionic surfactant, amphoteric surfactant, silicone surfactant, fluorocarbon surfactant, lubricant and mixtures thereof.

72. The process of claim 71 wherein the adjuvant is a cationic surfactant.

73. The process of claim 72 wherein the cationic surfactant is selected from group consisting of alkylamine ethoxylates, alkylamine quaternary amines, alkylamine acetates, amine oxides or combinations thereof.

74. The process of claim 70 wherein the weight ratio of total adjuvant to ammonium glyphosate is from about 1:9 to about 1:2.

75. The process of claim 70 wherein the portion of the adjuvant being added to the reactor to form the reaction mass is such that the weight ratio of adjuvant to glyphosate acid added to the reactor is at least about 1:250.

76. The process of claim 70 wherein the portion of the adjuvant added to the reactor to form the reaction mass is such that the weight ratio of adjuvant to glyphosate acid added to the reactor is from about 1:250 to about 1:2.

77. The process of claim 70 wherein the portion of the adjuvant added to the reactor to form the reaction mass is such that the weight ratio of adjuvant to glyphosate acid added to the reactor is from about 1:250 to about 1:10.

78. The process of claim 70 wherein the portion of the adjuvant added to the reactor to form the reaction mass is such that the weight ratio of adjuvant to glyphosate acid added to the reactor is from about 1:250 to about 1:25.

79. The process of claim 70 wherein the portion of the adjuvant added to the reactor to form the reaction mass is such that the weight ratio of adjuvant to glyphosate acid added to the reactor is from about 1:100 to about 1:50.

80. The process of claim 70 wherein the molar ratio of ammonia to glyphosate acid added to the reactor is from about 0.8 to about 1.25.

81. The process of claim 70 wherein the molar ratio of ammonia to glyphosate acid added to the reactor is from about 0.9 to about 1.1.

82. The process of claim 70 wherein the molar ratio of ammonia to glyphosate acid added to the reactor is from about 0.95 to about 1.05.

83. The process of claim 70 wherein the total amount of water added to the reactor is from about 13% to about 18% by weight of all of the glyphosate acid, ammonia, water and adjuvant added to the reactor.

84. The process of claim 70 wherein the ammonium glyphosate paste composition has a moisture content of from about 2% to about 20% by weight by weight.

85. The process of claim 70 wherein the ammonium glyphosate paste composition has a moisture content of from about 2% to about 15% by weight.

86. The process of claim 70 wherein the ammonium glyphosate paste composition has a moisture content of from about 2% to about 10% by weight.

87. The process of claim 70 wherein the ammonium glyphosate paste composition has a moisture content of from about 3% to about 5% by weight.

88. The process of claim 70 wherein all or part of the water in the reactor is introduced as moisture associated with the glyphosate acid and/or as the water component of aqueous ammonia or adjuvant.

89. The process of claim 70 wherein the ammonia is introduced as anhydrous ammonia.

90. The process of claim 89 wherein the ammonia is introduced as liquid anhydrous ammonia.

91. The process of claim 70 wherein the apertures in the screen have a diameter of from about 0.5 mm to about 2 mm.

92. The process of claim 70 wherein the apertures in the screen have a diameter of from about 0.6 mm to about 1.2 mm.

93. The process of claim 70 wherein addition of adjuvant to the reaction mass increases the throughput of the extruder by at least about 5%.

94. The process of claim 70 wherein addition of adjuvant to the reaction mass increases the throughput of the extruder by at least about 10%.

95. The process of claim 70 wherein addition of adjuvant to the reaction mass increases the throughput of the extruder by at least about 25%.

96. The process of claim 70 wherein addition of adjuvant to the reaction mass increases the throughput of the extruder by at least about 50%.

97. The process of claim 70 wherein addition of adjuvant to the reaction mass increases the throughput of the extruder by greater than about 50%.

98. The process of claim 70 further comprising classifying or milling the granules to remove or recycle granules, fragments of granules and aggregates of granules that are outside a desired size range.

99. The process of claim 70 wherein, if the moisture content of the ammonium glyphosate paste on completion of the reaction is a greater than about 10% by weight, heat and/or vacuum is applied to reduce the moisture content of the paste to about 5% to about 10% by weight prior to forming the extrudable ammonium glyphosate mixture.

100. The process of claim 70 wherein the extrudable ammonium glyphosate mixture is of a consistency such that the extrudate strands break spontaneously upon extrusion to form the granules.

101. The process of claim 70 further comprising breaking or cutting the extrudate strands to form the granules.

102. The process of claim 70 further comprising rolling and/or tumbling the moist granules to impart to the granules a more spherical shape and greater uniformity of size.

103. The process of claim 70 wherein the rate of formation of ammonium glyphosate paste is at least about 0.02 gram-moles/minute-liter of reactor volume.

104. The process of claim 70 wherein the rate of formation of ammonium glyphosate is at least about 0.05 gram-mole/minute-liter of reactor volume.

105. The process of claim 70 wherein the rate of formation of ammonium glyphosate is at least about 0.075 gram-moles/minute-liter of reactor volume.

106. The process of claim 70 wherein the rate of formation of ammonium glyphosate is at least about 0.1 gram-moles/minute-liter of reactor volume.

107. The process of claim 70 wherein the rate of formation of ammonium glyphosate is at least about 0.2 gram-moles/minute-liter of reactor volume.

108. The process of claim 70 wherein the rate of formation of ammonium glyphosate is at least about 0.3 gram-moles/minute-liter of reactor volume.

109. The process of claim 70 wherein the rate of formation of ammonium glyphosate paste is at least about 0.4 gram-moles/minute-liter of reactor volume.

110. The process of claim 1 wherein the particulate glyphosate acid, ammonia, water and adjuvant are added to the reactor in a manner such that the particulate glyphosate acid, water and adjuvant are mixed prior to substantial exposure of the glyphosate acid with the ammonia.

111. The process of claim 110 wherein the particulate glyphosate acid, water and adjuvant are pre-mixed before being introduced into the reactor.

112. The process of claim 38 wherein the particulate glyphosate acid, ammonia, water and adjuvant are added to the reactor in a manner such that the particulate glyphosate acid, water and adjuvant are mixed prior to substantial exposure of the glyphosate acid with the ammonia.

113. The process of claim 112 wherein the particulate glyphosate acid, water and adjuvant are pre-mixed before being introduced into the reactor.

114. The process of claim 70 wherein the particulate glyphosate acid, ammonia, water and adjuvant are added to the reactor in a manner such that the particulate glyphosate acid, water and adjuvant are mixed prior to substantial exposure of the glyphosate acid with the ammonia.

115. The process of claim 114 wherein the particulate glyphosate acid, water and adjuvant are pre-mixed before being introduced into the reactor.

116. The process of claim 15 wherein the adjuvant added to the reactor is a lubricant.

117. The process of claim 116 wherein the lubricant is a silicon oil.

118. The process of claim 117 wherein the silicon oil is polydimethylsiloxane.

119. The process of claim 71 wherein the adjuvant added to the ammonium glyphosate paste composition is lubricant.

120. The process of claim 119 wherein the lubricant is a silicon oil.

121. The process of claim 120 wherein the silicon oil is polydimethylsiloxane.

122. A method for preparing an extrudable ammonium glyphosate mixture comprising mixing a lubricant with an ammonium glyphosate paste composition having a moisture content of from about 2% to about 20% by weight.

123. The method of claim 122 wherein the lubricant is a silicon oil.

124. The method of claim 123 wherein the silicon oil is polydimethylsiloxane.

125. The method of claim 122 wherein the ammonium glyphosate paste composition has a moisture content of from about 2% to about 15% by weight.

126. The process of claim 122 wherein the ammonium glyphosate paste composition has a moisture content of from about 2% to about 10% by weight.

127. The process of claim 122 wherein the ammonium glyphosate paste composition has a moisture content of from about 3% to about 5% by weight.

* * * * *

UNITED STATES PATENT AND TRADEMARK OFFICE
CERTIFICATE OF CORRECTION

| | |
|---|---|
| PATENT NO. | : 6,734,142 B2 |
| APPLICATION NO. | : 10/122806 |
| DATED | : May 11, 2004 |
| INVENTOR(S) | : Massmann et al. |

It is certified that error appears in the above-identified patent and that said Letters Patent is hereby corrected as shown below:

Column 20, claim 22, line 47: the second "by weight" phrase should be deleted.

Column 21, claim 38, line 60: "(vi)" should read -- (iv) --.

Column 22, claim 41, line 23: "oxides or combinations" should read -- oxides and combinations --.

Column 24, claim 70, line 12: "(ix)" should read -- (iv) --.

Column 24, claim 73, line 46: "oxides or combinations" should read -- oxides and combinations --.

Column 28, claim 126, line 4: "The process of claim 122" should read -- The method of claim 122 --.

Column 28, claim 127, line 7: "The process of claim 122" should read -- The method of claim 122 --.

Signed and Sealed this

Twelfth Day of January, 2010

David J. Kappos
*Director of the United States Patent and Trademark Office*